(12) United States Patent
Foley

(10) Patent No.: US 7,173,162 B2
(45) Date of Patent: Feb. 6, 2007

(54) CORN PLANTS WITH IMPROVED QUALITY GRAIN TRAITS

(75) Inventor: Terry Foley, Williamsburg, IA (US)

(73) Assignee: Monsanto Technology, L.L.C., St. Louis, MO (US)

( * ) Notice: Subject to any disclaimer, the term of this patent is extended or adjusted under 35 U.S.C. 154(b) by 593 days.

(21) Appl. No.: 10/330,491

(22) Filed: Dec. 27, 2002

(65) Prior Publication Data

US 2003/0182697 A1 Sep. 25, 2003

Related U.S. Application Data

(60) Provisional application No. 60/343,965, filed on Dec. 28, 2001.

(51) Int. Cl.
*A01H 1/00* (2006.01)
*A01H 1/02* (2006.01)
*C12P 7/64* (2006.01)

(52) U.S. Cl. ............... 800/275; 800/272; 800/274; 800/264; 800/320.1

(58) Field of Classification Search ............ 800/272, 800/274, 275, 264, 320.1
See application file for complete search history.

(56) References Cited

U.S. PATENT DOCUMENTS

| | | | | |
|---|---|---|---|---|
| 4,517,763 | A | 5/1985 | Beversdorf et al. | 47/58 |
| 4,642,411 | A | 2/1987 | Hibberd et al. | 800/1 |
| 4,658,084 | A | 4/1987 | Beversdorf et al. | 800/1 |
| 4,658,085 | A | 4/1987 | Beversdorf et al. | 800/1 |
| 4,677,246 | A | 6/1987 | Armond et al. | 800/1 |
| 4,731,499 | A | 3/1988 | Puskaric et al. | 800/1 |
| 5,082,993 | A | 1/1992 | Strissel et al. | 800/200 |
| 5,276,263 | A | 1/1994 | Foley | 800/200 |
| 5,704,160 | A | 1/1998 | Bergquist et al. | 800/264 |
| 5,706,603 | A | 1/1998 | Bergquist et al. | 47/58 |
| 5,763,755 | A * | 6/1998 | Carlone | 800/320.1 |
| 5,850,009 | A * | 12/1998 | Kevern | 800/271 |
| 5,922,934 | A | 7/1999 | Bergquist et al. | 800/320.1 |
| 5,986,182 | A | 11/1999 | Thompson et al. | 800/320.1 |
| 6,242,674 | B1 | 6/2001 | Bergquist et al. | 800/320.1 |
| 6,248,939 | B1 | 6/2001 | Leto et al. | 800/320.1 |

OTHER PUBLICATIONS

Goldman et al. Crop Science 34(4): 908-915 (1994).*
Stuber et al. Crop Science 17(4): 503-506 (Jul.-Aug. 1977).*
Melchinger et al. Theoretical and Applied Genetics 72(2): 231-239 (1986).*
Murray et al. pp. 72-87 In: Proc. 43$^{rd}$ Annual Corn & Sorghum Industry Research, Wilkinson et al, eds, American Seed Trade Association (1988).*
Armstrong & Green, "Establishment and maintenance of friable embryogenic maize callus and the involvement of L-Proline," *Planta*, 164:207-214, 1985.
Duvick, "Genetic Contributions to Yield Gains of U.S. Hybrid Maize, 1930 to 1980," *Genetic Contributions to Yield Gains of Five Major Crop Plants*: Proceedings of a Symposium sponsored by Div. C-1, Crop Science Society of America, Dec. 2, 1981 in Atlanta, Georgia; W.R. Fehr, Crop Science Society of America and American Society of Agronomy, Madison, Wisconsin, pp. 15-47.
Fehr (ed.), "Backcross method," *Principles of Cultivar Development, vol. 1: Theory and Technique*, Ch. 28, pp. 360-376, 1987.
Hallauer et al., "Corn Breeding," *Corn and Corn Improvement*, eds., Sprague et al., Madison, Wisconsin, Ch. 8, pp. 463-564, 1988.
Larson & Hanway, "Corn Production," *Corn and Corn Improvement*, ed. G.F. Sprague, No. 18 in Agronomy Series, American Society of Agronomy, Inc., Madison, Wisconsin, Ch. 8, pp. 625-669, 1977.
Maize Genetics Cooperation Newsletter, 70:94, Mar. 15, 1996.
Meghji et al., "Inbreeding depression, inbred and hybrid grain yields, and other traits of maize genotypes representing three eras," *Crop Science*, 24:545-549, 1984.
Poehlman et al., *Breeding Field Crops*, 4$^{th}$ edition, Iowa State University Press, Ames, IA, pp. 172-175, 1995.
Poehlman, *Breeding Field Crops*, 3rd ed., AVI Publishing Company, Westport, Connecticut, pp. 469-481, 1987.
Rieger et al., *Glossary of Genetics and Cytogenetics, Classical and Molecular*, Springer-Verlag, Berlin, p. 116, 1976.
Sprague & Eberhart, "Corn Breeding," *Corn and Corn Improvements*, ed. G.F. Sprague, No. 18 in Agronomy Series, American Society of Agronomy, Inc., Madison, Wisconsin, Ch. 6, pp. 305-323, 1977.
Sprague and Dudley (eds.), *Corn and Corn Improvement*, 3$^{rd}$ edition, Crop Science of America, Inc., and Soil Science of America, Inc. Madison, Wisconsin, pp. 881-883, 901-918, 1988.
Troyer, "A retrospective view of corn genetic resources," *Journal of Heredity*, 81:17-24, 1990.
Wright, "Commercial hybrid seed," *Hybridization of Crop Plants*, Fehr et al., eds. Am. Soc. of agron.-Crop Sci. Soc. of Am., Madison, Wisconsin, Ch. 8, pp. 161-176, 1980.
Wych, "Production of hybrid seed corn," *Corn and Corn Improvement, eds.*, Sprague et al, editors, Madison, Wisconsin, Ch. 9, pp. 565-607, 1988.

* cited by examiner

Primary Examiner—David T. Fox
(74) Attorney, Agent, or Firm—Fulbright & Jaworski L.L.P.

(57) ABSTRACT

According to the invention, there are provided methods for producing novel corn plants with enhanced quality grain traits comprising using the corn accession REN 001 and plants derived therefrom. Also provided by the invention are the plants produced by such methods. The invention further provides methods for producing corn grain with improved quality grain traits comprising pollinating elite hybrid corn varieties with pollen from the corn accession REN 001 and plants produced therefrom.

20 Claims, No Drawings

CORN PLANTS WITH IMPROVED QUALITY GRAIN TRAITS

BACKGROUND OF THE INVENTION

This application claims the priority of U.S. Provisional Patent Application Ser. No. 60/343,965, filed Dec. 28, 2001, the entire disclosure of which is specifically incorporated herein by reference.

FIELD OF THE INVENTION

The present invention relates generally to the field of corn breeding. In particular, the invention relates to methods of using the corn accession designated REN 001.

DESCRIPTION OF RELATED ART

The goal of field crop breeding is to combine various desirable traits in a single variety/hybrid. Such desirable traits include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant. Corn plants (*Zea mays* L.) can be bred by both self-pollination and cross-pollination. Both types of pollination involve the corn plant's flowers. Corn has separate male and female flowers on the same plant, located on the tassel and the ear, respectively. Natural pollination occurs in corn when wind blows pollen from the tassels to the silks that protrude from the tops of the ear shoot.

Plants that have been self-pollinated and selected for type over many generations become homozygous at almost all gene loci and produce a uniform population of true breeding progeny, a homozygous plant. A cross between two such homozygous plants produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform corn plant hybrids requires the development of homozygous inbred plants, the crossing of these inbred plants, and the evaluation of the crosses. Pedigree breeding and recurrent selection are examples of breeding methods used to develop inbred plants from breeding populations. Those breeding methods combine the genetic backgrounds from two or more inbred plants or various other broad-based sources into breeding pools from which new inbred plants are developed by selfing and selection of desired phenotypes. The new inbreds are crossed with other inbred plants and the hybrids from these crosses are evaluated to determine which of those have commercial potential.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. After at least five generations, the inbred plant is considered genetically pure.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

A single cross hybrid corn variety is the cross of two inbred plants, each of which has a genotype that complements the genotype of the other. The hybrid progeny of the first generation is designated $F_1$. Typically, $F_1$ hybrids are more vigorous than their inbred parents. This hybrid vigor, or heterosis, is manifested in many polygenic traits, including markedly improved yields, better stalks, better roots, better uniformity and better insect and disease resistance. In the development of hybrids only the $F_1$ hybrid plants are typically sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)× (C×D).

The development of a hybrid corn variety typically involves three steps: (1) the selection of plants from various germplasm pools; (2) the selfing of the selected plants for several generations to produce a series of inbred plants, which, although different from each other, each breed true and are highly uniform; and (3) crossing the selected inbred plants with unrelated inbred plants to produce the hybrid progeny ($F_1$). During the inbreeding process in corn, the vigor of the plants decreases. Vigor is restored when two unrelated inbred plants are crossed to produce the hybrid progeny ($F_1$). An important consequence of the homozygosity and homogeneity of the inbred plants is that the hybrid between any two inbreds is always the same. Once the inbreds that give a superior hybrid have been identified, hybrid seed can be reproduced indefinitely as long as the homogeneity of the inbred parents is maintained. Conversely, much of the hybrid vigor exhibited by $F_1$ hybrids is lost in the next generation ($F_2$). Consequently, seed from hybrid varieties is not used for planting stock. It is not generally beneficial for farmers to save seed of $F_1$ hybrids. Rather, farmers purchase $F_1$ hybrid seed for planting every year.

North American farmers plant tens of millions of acres of corn at the present time and there are extensive national and international commercial corn breeding programs. A continuing goal of these corn breeding programs is to develop corn hybrids that are based on stable inbred plants and have one or more desirable characteristics. To accomplish this goal, the corn breeder must select and develop superior inbred parental plants.

SUMMARY OF THE INVENTION

In one aspect, the invention provides a method of producing a corn plant with at least a first improved quality grain trait comprising the steps of: (a) crossing a corn plant of corn accession REN 001 with a second corn plant or with itself; and (b) selecting a progeny corn plant resulting from said crossing and having at least one improved quality grain trait. In certain embodiments of the invention, one of the plants used for crossing is rendered male sterile prior to the crossing, and may include a nuclear or cytoplasmic gene conferring male sterility. Crossing can be carried out by any method, including hand pollinating or allowing natural pollination to occur.

In one embodiment of the invention, a corn plant prepared by the methods of the invention may comprise an improved quality grain trait selected from the group consisting of: oil content in excess of about 6% of the seed dry matter, protein content in excess of about 10% of the seed dry matter, improved oil quality, enhanced oxidative stability of the oil, reduced polyunsaturated fatty acids in the oil, oleic acid content in excess of about 35% of the total fatty acids of the oil, lysine content in excess of about 0.32% of the seed dry matter, and tryptophan content in excess of about 0.08% of the seed dry matter. Alternatively, the corn plant may comprise one or more traits selected from the group consisting of: an oleic acid content in excess of about 28%, about 30%, about 32% and about 35% of the total fatty acids of the oil; lysine content in excess of about 0.25%, about 0.28%, about 0.30% or about 0.32% of the seed dry matter; and tryptophan content of grain in excess of about 0.05%, about 0.06%, about 0.07% or about 0.08% of the seed dry matter.

In further embodiments of the invention, the second corn plant may be inbred or hybrid, including a synthetic hybrid plant and may be genetically heterogeneous. The corn plant prepared by crossing a corn plant of corn accession REN 001 with a second corn plant or with itself may be used as a pollen donor and the second corn plant a pollen receptor or may be used as the pollen receptor and the second corn plant used as a pollen donor.

In the methods of the invention, crossing may comprise (a) obtaining a population of seed of corn accession REN 001; (b) selecting a seed having an enlarged embryo relative to seeds in the population; and (c) growing the seed to produce a corn plant of corn accession REN 001. As used herein, the term "enlarged" refers to those embryos larger than the average embryo size within the population or, alternatively, larger than about 20%, about 40%, about 60%, about 80%, about 90% and about 95% of seeds in the population.

The methods of the invention may further comprise the steps of: (c) crossing the progeny corn plant with itself or a third plant to produce a progeny plant of a subsequent generation and may still further comprise the steps of: (d) crossing the progeny plant of a subsequent generation with itself or a second plant; and (e) repeating steps (c) and (d) for an additional 3–10 generations to produce an inbred corn plant derived from the corn accession REN 001. In the method, the progeny plant of a subsequent generation may be selected for crossing based on the presence of at least a first enhanced quality grain trait and may further be selected at some or all generations for crossing based on the presence of at least a first enhanced quality grain trait. The enhanced quality grain trait may be, in one embodiment of the invention, selected from the group consisting of: oil content in excess of about 6% of the seed dry matter, protein content in excess of about 10% of the seed dry matter, improved oil quality, enhanced oxidative stability of the oil, reduced polyunsaturated fatty acids in the oil, oleic acid content in excess of about 35% of the total fatty acids of the oil, lysine content in excess of about 0.32% of the seed dry matter, and tryptophan content in excess of about 0.08% of the seed dry matter.

In another aspect, the invention provides a corn plant produced by a method of the invention and that comprises at least two of the following traits of the corn accession REN 001: oil content in excess of about 6% of the seed dry matter, protein content in excess of about 10% of the seed dry matter, improved oil quality, enhanced oxidative stability of the oil, reduced polyunsaturated fatty acids in the oil, oleic acid content in excess of about 35% of the total fatty acids of the oil, lysine content in excess of about 0.32% of the seed dry matter, and tryptophan content in excess of about 0.08% of the seed dry matter. In further embodiments of the invention, the corn plant may comprise less than all of the traits of corn plant REN 001, and may, in certain embodiments of the invention, comprise only about 3, about 4, about 5, about 6, about 7, about 8, or about 9 of the foregoing traits of REN 001.

In still yet another aspect, the invention provides a seed composition comprising seeds of corn accession REN 001 or a corn plant prepared by crossing a corn plant of corn accession REN 001 with a second corn plant or with itself. Seed compositions are also provided comprising such seeds randomly intermixed with seeds of an agronomically elite hybrid corn variety, wherein the hybrid corn variety is genetically male sterile, wherein the seeds of corn accession REN 001 are present in a ratio of less than about 1 to about 3. In certain further embodiments of the invention, a population of seeds of corn accession REN 001 is provided. The seed composition may be essentially free of other seed and, for example, may be defined as comprising at least about 70%, 80%, 90%, 95%, 98%, 99% or 100% REN 001 seed. In other embodiments of the invention, populations of REN 001 seed are provided consisting essentially of REN 001 seed. Such populations may, in one embodiment of the invention, be distinguishable from other seed populations based on the enlarged embryo size of seeds in a collection of REN 001 seed.

In still yet another aspect, the invention provides a process of producing corn grain, comprising: (a) planting seeds of first and second corn plants in pollinating proximity; wherein the first plant is an agronomically elite variety and wherein the second plant is a corn plant of the accession REN 001 or a corn plant prepared by crossing a corn plant of corn accession REN 001 with a second corn plant or with itself; (b) growing the first and second plants to maturity; (c) allowing pollen from the second plant to pollinate the first plant; and (d) collecting grain that forms on at least the first plant. The planting may comprise planting a population of seeds comprising seeds of the first and second corn plants. The collecting may comprise harvesting grain formed on the first corn plant and the second corn plant. In particular embodiments of the invention, the first corn plant is genetically male sterile.

In still yet another aspect of the invention, plants used with or prepared by the methods of the invention may further comprise, or have, a cytoplasmic or nuclear factor that is capable of conferring male sterility or otherwise preventing self-pollination, such as by self-incompatibility. A cytoplasmically-inherited trait is passed to progeny through the female parent in a particular cross. An exemplary cytoplasmically-inherited trait is the male sterility trait. Cytoplasmic-male sterility (CMS) is a pollen abortion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus, and continue to be male sterile in the next generation. The male fertility of a CMS plant can be restored by a restorer version of the same variety, which must have the restorer gene(s) in the nucleus. With the restorer gene(s) in the nucleus, the offspring of the male-sterile plant can produce normal pollen grains and propagate. A cytoplasmically inherited trait may be a naturally occurring maize trait or a trait introduced through genetic transformation techniques.

DETAILED DESCRIPTION OF THE INVENTION

I. Definitions of Plant Characteristics

Barren Plants: Plants that are barren, i.e., lack an ear with grain, or have an ear with only a few scattered kernels.

Cg: *Colletotrichum graminicola* rating. Rating times 10 is approximately equal to percent total plant infection.

CLN: Corn Lethal Necrosis (combination of Maize Chlorotic Mottle Virus and Maize Dwarf Mosaic virus) rating: numerical ratings are based on a severity scale where 1=most resistant to 9=susceptible.

Cn: *Corynebacterium nebraskense* rating. Rating times 10 is approximately equal to percent total plant infection.

Cz: *Cercospora zeae-maydis* rating. Rating times 10 is approximately equal to percent total plant infection.

Dgg: *Diatraea grandiosella* girdling rating (values are percent plants girdled and stalk lodged).

Dropped Ears: Ears that have fallen from the plant to the ground.

Dsp: Diabrotica species root ratings (1=least affected to 9=severe pruning).

Ear-Attitude: The attitude or position of the ear at harvest scored as upright, horizontal, or pendant.

Ear-Cob Color: The color of the cob, scored as white, pink, red, or brown.

Ear-Cob Diameter: The average diameter of the cob measured at the midpoint.

Ear-Cob Strength: A measure of mechanical strength of the cobs to breakage, scored as strong or weak.

Ear-Diameter: The average diameter of the ear at its midpoint.

Ear-Dry Husk Color: The color of the husks at harvest scored as buff, red, or purple.

Ear-Fresh Husk Color: The color of the husks 1 to 2 weeks after pollination scored as green, red, or purple.

Ear-Husk Bract: The length of an average husk leaf scored as short, medium, or long.

Ear-Husk Cover: The average distance from the tip of the ear to the tip of the husks. Minimum value no less than zero.

Ear-Husk Opening: An evaluation of husk tightness at harvest scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence scored as green-yellow, yellow, pink, red, or purple.

Ear-Taper (Shape): The taper or shape of the ear scored as conical, semi-conical, or cylindrical.

Ear-Weight: The average weight of an ear.

Early Stand: The percent of plants that emerge from the ground as determined in the early spring.

ER: Ear rot rating (values approximate percent ear rotted).

Final Stand Count: The number of plants just prior to harvest.

GDUs: Growing degree units are calculated herein by the Barger Method, where the heat units for a 24-h period are calculated as GDUs=[(Maximum daily temperature+Minimum daily temperature)/2]−50. The highest maximum daily temperature used is 86° F. and the lowest minimum temperature used is 50° F.

GDUs to Shed: The number of growing degree units (GDUs) or heat units required for an inbred line or hybrid to have approximately 50% of the plants shedding pollen as measured from time of planting. GDUs to shed is determined by summing the individual GDU daily values from planting date to the date of 50% pollen shed.

GDUs to Silk: The number of growing degree units for an inbred line or hybrid to have approximately 50% of the plants with silk emergence as measured from time of planting. GDUs to silk is determined by summing the individual GDU daily values from planting date to the date of 50% silking.

Hc2: *Helminthosporium carbonum* race 2 rating. Rating times 10 is approximately equal to percent total plant infection.

Hc3: *Helminthosporium carbonum* race 3 rating. Rating times 10 is approximately equal to percent total plant infection.

Hm: *Helminthosporium maydis* race 0 rating. Rating times 10 is approximately equal to percent total plant infection.

Ht1: *Helminthosporium turcicum* race 1 rating. Rating times 10 is approximately equal to percent total plant infection.

Ht2: *Helminthosporium turcicum* race 2 rating. Rating times 10 is approximately equal to percent total plant infection.

HtG: Chlorotic-lesion type resistance. +=indicates the presence of Ht chlorotic-lesion type resistance; −=indicates absence of Ht chlorotic-lesion type resistance; and +/−=indicates segregation of Ht chlorotic-lesion type resistance. Rating times 10 is approximately equal to percent total plant infection.

Kernel-Aleurone Color: The color of the aleurone scored as white, pink, tan, brown, bronze, red, purple, pale purple, colorless, or variegated.

Kernel-Cap Color: The color of the kernel cap observed at dry stage, scored as white, lemon-yellow, yellow, or orange.

Kernel-Endosperm Color: The color of the endosperm scored as white, pale yellow, or yellow.

Kernel-Endosperm Type: The type of endosperm scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp scored as colorless, red-white crown, tan, bronze, brown, light red, cherry red, or variegated.

Kernel-Row Direction: The direction of the kernel rows on the ear scored as straight, slightly curved, spiral, or indistinct (scattered).

Kernel-Row Number: The average number of rows of kernels on a single ear.

Kernel-Side Color: The color of the kernel side observed at the dry stage, scored as white, pale yellow, yellow, orange, red, or brown.

Kernel-Thickness: The distance across the narrow side of the kernel.

Kernel-Type: The type of kernel scored as dent, flint, or intermediate.

Kernel-Weight: The average weight of a predetermined number of kernels.

Kernel-Width: The distance across the flat side of the kernel.

Kz: *Kabatiella zeae* rating. Rating times 10 is approximately equal to percent total plant infection.

Leaf-Angle: Angle of the upper leaves to the stalk scored as upright (0 to 30 degrees), intermediate (30 to 60 degrees), or lax (60 to 90 degrees).

Leaf-Color: The color of the leaves 1 to 2 weeks after pollination scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination. Rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, scored as absent, basal-weak, basal-strong, weak or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf measured at its widest point.

LSS: Late season standability (values times 10 approximate percent plants lodged in disease evaluation plots).

Moisture: The moisture of the grain at harvest.

On1: *Ostrinia nubilalis* 1st brood rating (1=resistant to 9=susceptible).

On2: *Ostrinia nubilalis* 2nd brood rating (1=resistant to 9=susceptible).

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging: Root lodging is the percentage of plants that root lodge. A plant is counted as root lodged if a portion of the plant leans from the vertical axis by approximately 30 degrees or more.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale, where 1 equals best. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Sr: *Sphacelotheca reiliana* rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes With Brace Roots: The average number of nodes having brace roots per plant.

Stalk-Plant Height: The average height of the plant as measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity). It is usually recorded at the time the ear husks of most entries within a trial have turned a mature color. Scoring is on a 1 to 9 basis where 1 equals best.

STR: Stalk rot rating (values represent severity rating of 1=25% of inoculated internode rotted to 9=entire stalk rotted and collapsed).

SVC: Southeastern Virus Complex (combination of Maize Chlorotic Dwarf Virus and Maize Dwarf Mosaic Virus) rating; numerical ratings are based on a severity scale where 1=most resistant to 9=susceptible (1988 reactions are largely Maize Dwarf Mosaic Virus reactions).

Tassel-Anther Color: The color of the anthers at 50% pollen shed scored as green-yellow, yellow, pink, red, or purple.

Tassel-Attitude: The attitude of the tassel after pollination scored as open or compact.

Tassel-Branch Angle: The angle of an average tassel branch to the main stem of the tassel scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume scored as present or absent.

Tassel-Glume Color: The color of the glumes at 50% shed scored as green, red, or purple.

Tassel-Length: The length of the tassel measured from the base of the bottom tassel branch to the tassel tip.

Tassel-Peduncle Length: The average length of the tassel peduncle, measured from the base of the flag leaf to the base of the bottom tassel branch.

Tassel-Pollen Shed: A visual rating of pollen shed determined by tapping the tassel and observing the pollen flow of approximately five plants per entry. Rated on a 1 to 9 scale where 9=sterile, 1=most pollen.

Tassel-Spike Length: The length of the spike measured from the base of the top tassel branch to the tassel tip.

Test Weight: Weight of the grain in pounds for a given volume (bushel) adjusted to 15.5% moisture.

Yield: Yield of grain at harvest adjusted to 15.5% moisture.

II. Other Definitions

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Chromatography: A technique wherein a mixture of dissolved substances are bound to a solid support followed by passing a column of fluid across the solid support and varying the composition of the fluid. The components of the mixture are separated by selective elution.

Crossing: The pollination of a female flower of a corn plant with pollen from the same plant or from any other plant of the same or a different genotype, thereby resulting in the production of seed from the flower.

Cross-pollination: Fertilization by the union of two gametes from different plants.

Diploid: A cell or organism having two sets of chromosomes.

Electrophoresis: A process by which particles suspended in a fluid or a gel matrix are moved under the action of an electrical field, and thereby separated according to their charge and molecular weight. This method of separation is well known to those skilled in the art and is typically applied to separating various forms of enzymes and of DNA fragments produced by restriction endonucleases.

Emasculate: The removal of plant male sex organs or the inactivation of the organs with a chemical agent or a cytoplasmic or nuclear genetic factor conferring male sterility.

Enzymes: Molecules that can act as catalysts in biological reactions.

$F_1$ Hybrid: The first generation progeny of the cross of two plants.

Genetic Complement: An aggregate of nucleotide sequences, the expression of which sequences defines the phenotype in corn plants, or components of plants including cells or tissue.

Genotype: The genetic constitution of a cell or organism.

Haploid: A cell or organism having one set of the two sets of chromosomes in a diploid.

Isozymes: Detectable variants of an enzyme, the variants catalyzing the same reaction(s) but differing from each other, e.g., in primary structure and/or electrophoretic mobility. The differences between isozymes are under single gene, codominant control. Consequently, electrophoretic separation to produce band patterns can be equated to different alleles at the DNA level. Structural differences that do not alter charge cannot be detected by this method.

Isozyme typing profile: A profile of band patterns of isozymes separated by electrophoresis that can be equated to different alleles at the DNA level.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Metaxenia: An effect exerted on the phenotype of the embryo and associated diploid tissues of a seed by the genotype contributed by the pollen.

REN 001: The corn plant accession from which seeds having ATCC Accession No. PTA-3822 were obtained, as well as plants grown from those seeds.

Phenotype: The detectable characteristics of a cell or organism, which characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

SSR profile: A profile of simple sequence repeats used as genetic markers and scored by gel electrophoresis following PCR™ amplification using flanking oligonucleotide primers.

Self-pollination: The transfer of pollen from the anther to the stigma of the same plant.

Single Locus Converted (Conversion) Plant: Plants that are developed by a plant breeding technique called backcrossing wherein essentially all of the desired morphological and physiological characteristics of a variety are recovered in addition to the characteristics conferred by the single locus transferred into the variety via the backcrossing technique. A single locus may comprise one gene, or in the case of transgenic plants, one or more transgenes integrated into the host genome at a single site (locus).

Substantially equivalent: The modifier "substantially equivalent" as used with respect to a first numerical value, such as that associated with a quantitative trait, for example, is used to include those numerical values that, when compared to the first numerical value, do not show statistical differences of their respective means.

Tissue Culture: A composition comprising isolated cells of the same or a different type or a collection of such cells organized into parts of a plant.

Transgene: A genetic sequence that has been introduced into the nuclear or chloroplast genome of a maize plant by a genetic transformation technique.

Xenia: An effect exerted on the phenotype of the endosperm of a seed by the genotype contributed by the pollen.

III. Corn Accession REN 001

In accordance with one aspect of the present invention, methods are provided of using the corn plant accession designated REN 001, including lines produced by selfing or outcrossing plants of corn accession REN 001. In certain aspects of the invention, methods are provided for creating a new plant variety with the accession REN 001. For example, inbred corn plants can be produced by planting the seeds of the corn plant accession REN 001, selfing or outcrossing the plants and growing resulting corn plants under self-pollinating or sib-pollinating conditions with adequate isolation using standard techniques well known to an artisan skilled in the agricultural arts. Seeds can be harvested from such a plant using standard, well known procedures.

A. Phenotypic Description

In accordance with another aspect of the present invention, there is provided a corn plant having the physiological and morphological characteristics of corn plant accession REN 001. A description of the physiological and morphological characteristics of corn plant accession REN 001 is presented in Table 1.

TABLE 1

Physiological and Morphological Characteristics for the REN 001 Phenotype

| MATURITY: | Days | Heat Units |
|---|---|---|
| From emergence to 50% of plants in silk: | 78 | 1471 |
| From emergence to 50% of plants in pollen | 77 | 1451 |

$$\text{Heat Units:} = \frac{[\text{Max. Temp. } (\leq 86° \text{ F.}) + \text{Min. Temp.} (\geq 50° \text{F.})]}{2} - 50$$

PLANT:

Plant Height (to tassel tip): 222.0 cm
Ear Height (to base of top ear): 119.0 cm
Average number of Tillers: 0
Average Number of Ears per Stalk: 1
Anthocyanin of Brace Roots: Absent

LEAF:

Width of Ear Node Leaf: 9.0 cm
Length of Ear Node Leaf: 74.0 cm
Number of leaves above top ear: 5
Leaf Angle (from 2nd Leaf above ear at anthesis to Stalk above leaf): 28°
Leaf Color: Medium Green—Munsell Color Code 5 GY 4/4
Leaf Sheath Pubescence (Rate on scale from 1 = none to 9 = like peach fuzz): 2
Marginal Waves (Rate on scale from 1 = none to 9 = many): 8
Longitudinal Creases (Rate on scale from 1 = none to 9 = many): 4

TABLE 1-continued

Physiological and Morphological Characteristics for the REN 001 Phenotype

TASSEL:

Number of Lateral Branches: 6
Branch Angle from Central Spike: 15°
Tassel Length (from top leaf collar to tassel top): 38.0 cm
Pollen Shed (Rate on scale from 0 = male sterile to 9 = heavy shed): 6
Anther Color: Green-Yellow—Munsell Color Code 2.5 GY 7/6
Glume Color: Green—Munsell Color Code 5 GY 5/8
Bar Glumes: Absent EAR: (Unhusked Data)

Silk Color (3 days after emergence): Light Green—Munsell Color Code 2.5 GY 8/6
Fresh Husk Color (25 days after 50% silking): Light Green—Munsell Color Code 2.5 GY 7/6
Dry Husk Color (65 days after 50% silking): Buff—Munsell Color Code 7.5 YR 7/4
Husk Extension: Short (ears exposed)

EAR: (Husked Ear Data)

Ear Length: 10.0 cm
Ear Diameter at mid-point: 41.0 mm
Ear Weight: 45.0 gm
Number of Kernel Rows: 16
Kernel Rows: Distinct
Shank Length: 12.0 cm
Ear Taper: Average KERNEL: (Dried)

Kernel Length: 10.0 mm
Kernel Width: 7.0 mm
Kernel Thickness: 6.0 mm
Aleurone Color Pattern: Homozygous

COB:

Cob Diameter at Mid-Point: 3.0

*These are typical values. Values may vary due to environment. Other values that are substantially equivalent are also within the scope of the invention.

An analysis of the quality grain traits of accession REN 001 was carried out. As can be seen below in Tables 2–5, the analysis demonstrated that REN 001 exhibits markedly enhanced quality grain traits relative to the comparative varieties.

TABLE 2

Grain Traits for REN 001 and Selected Varieties*

| Strain Id | Germ (Mg) | Endosperm (Mg) | Germ Oil % | Endosperm Oil % | Combined Wt (Mg) | Composite Oil % | Whole Kernel (Mg) | Whole Kernel Oil % |
|---|---|---|---|---|---|---|---|---|
| REN 001 | 291.70 | 607.00 | 61.88 | 5.65 | 898.70 | 23.90 | 836.80 | 17.24 |
| IL. REV. HIGH OIL UI 1994 BULK | 171.30 | 820.10 | 32.16 | 0.84 | 991.40 | 6.25 | 1192.10 | 4.62 |
| IL. SWITCHBACK HIGH OIL UI 1995 BULK | 213.80 | 502.00 | 48.30 | 1.43 | 715.80 | 15.43 | 712.40 | 13.89 |
| IL. HIGH OIL UI 1975 (INC 1981) | 258.00 | 540.20 | 33.20 | 4.34 | 798.20 | 13.67 | 815.80 | 15.77 |
| IL. HIGH PROTEIN UI 1964 (INC 1979) | 134.00 | 655.30 | 37.17 | 1.40 | 789.30 | 7.47 | 731.00 | 4.61 |

TABLE 2-continued

Grain Traits for REN 001 and Selected Varieties*

| Strain Id | Germ (Mg) | Endosperm (Mg) | Germ Oil % | Endosperm Oil % | Combined Wt (Mg) | Composite Oil % | Whole Kernel (Mg) | Whole Kernel Oil % |
|---|---|---|---|---|---|---|---|---|
| IL. HIGH PROTEIN UI 1976 (INC 1987) | 95.00 | 457.10 | 31.55 | 1.58 | 552.10 | 6.74 | 555.00 | 4.63 |
| IL. HIGH PROTEIN UI 1986 (INC 1987) | 108.00 | 482.00 | 30.60 | 1.37 | 590.00 | 6.72 | 648.00 | 4.46 |

*Values are for five pooled kernels. These are typical values. Values may vary due to environment. Other values that are substantially equivalent are also within the scope of the invention.

TABLE 3

Oil Quality Grain Characteristics of REN 001 and Selected Varieties*

| STRAIN | Palmitic Acid | Palmitoleic Acid | Stearic Acid | Oleic Acid |
|---|---|---|---|---|
| REN 001 | 18.98 | 0.22 | 3.70 | 54.25 |
| IL. REV. HIGH PROTEIN UI 1995 BULK | 3.07 | 0.08 | 0.36 | 7.45 |
| IL. SWITCHBACK HIGH OIL UI 1995 BULK | 12.81 | 0.24 | 2.05 | 33.69 |
| IL. HIGH OIL UI 1975 (INC 1981) | 16.95 | 0.29 | 2.68 | 45.24 |
| IL. HIGH PROTEIN UI 1964 (INC 19750 | 4.34 | 0.09 | 0.49 | 8.90 |
| IL. HIGH PROTEIN UI 1976 (INC 1987) | 3.31 | 0.07 | 0.40 | 8.36 |
| IL. HIGH PROTEIN UI 1986 (INC 1987) | 3.91 | 0.07 | 0.47 | 8.38 |

*Values are for weight (mg) of individual fatty acids for five pooled kernels. These are typical values. Values may vary due to environment. Other values that are substantially equivalent are also within the scope of the invention.

TABLE 4

Oil Quality Grain Characteristics of a Selected REN 001-Derived Variety*

| Sample Analysis | CRGX 29204 | Crude Commodity Oil |
|---|---|---|
| C16:0 - Palmitic | 11.84 | 10.91 |
| C18:0 - Stearic | 2.47 | 1.83 |
| C18:1, 9c - Oleic | 35.65 | 27.79 |
| C18:1, 11c | 0.58 | 0.57 |
| C18:2 - Linoleic | 47.26 | 56.32 |
| C18:3 - Linolenic | 0.69 | 0.94 |

*Values are by wt % and based on kernel oil.. These are typical values. Values may vary due to environment. Other values that are substantially equivalent are also within the scope of the invention. CRGX 29204 was derived from a cross of the lines LH195 × BHO and HOI001.

TABLE 5

Quality Grain Traits in Hybrids Pollinated With a REN 001-Derived Line Versus Selected Selfed Hybrids*

| Grain Parent | Pollen | Crude Protein | Cystein | Methionine |
|---|---|---|---|---|
| LH195 × LH59 | HOI001 | 14.56 | 0.301 | 0.322 |
| LH212 × LH204 | HOI001 | 10.90 | 0.224 | 0.241 |
| LH198 × LH168 | HOI001 | 12.42 | 0.259 | 0.288 |
| LH236 × LH286 | HOI001 | 13.55 | 0.266 | 0.265 |
| LH192 × LH82 | HOI001 | 12.59 | 0.239 | 0.241 |
| LH198 × LH185 | HOI001 | 15.48 | 0.332 | 0.356 |
| REN 001 | HOI001 | 13.65 | 0.302 | 0.393 |
| LH200 × LH172 | Self | 9.99 | 0.216 | 0.237 |
| LH195 × LH265 | Self | 9.08 | 0.203 | 0.218 |
| LH243 × LH265 | Self | 10.18 | 0.213 | 0.260 |
| LH300 × LH176 | Self | 11.24 | 0.249 | 0.282 |

*Values are by wt %. These are typical values. Values may vary due to environment. Other values that are substantially equivalent are also within the scope of the invention.

B. Deposit Information

A representative deposit of 2500 seeds of the corn accession designated REN 001 was made with the American Type Culture Collection (ATCC), 10801 University Blvd., Manassas, Va. on Jan. 10, 2002. Those deposited seeds have been assigned ATCC Accession No. PTA-3822. The deposit was made in accordance with the terms and provisions of the Budapest Treaty relating to deposit of microorganisms and was made for a term of at least thirty (30) years and at least five (05) years after the most recent request for the furnishing of a sample of the deposit is received by the depository, or for the effective term of the patent, whichever is longer, and will be replaced if it becomes non-viable during that period.

IV. Processes of Preparing Corn Plants and the Corn Plants Produced by Such Crosses One aspect of the current invention provides methods for the creation of novel corn plants having enhanced quality grain traits. For example, in one aspect of the invention, a corn plant of accession REN 001 may be crossed with itself or with any second plant and the resulting plants may then be used for further breeding. For example, the plants may be each selfed for about 2 to 10 generations, thereby providing distinct, pure-breeding inbred lines. As desired, selections for one or more traits may be made at each generation. As such, it will be understood to those of skill in the art that, using standard breeding techniques, all of the traits of the corn accession REN 001 can be selected from a population of seed produced by selfing or outcrossing corn accession REN 001. For example, by growing a population of seed produced by crossing accession REN 001 with a second line under self pollinating conditions over several generations and selecting for the traits of accession REN 001, essentially all of traits of accession REN 001 can be recovered.

Novel lines produced in accordance with the invention posses markedly improved quality grain traits relative to prior conventional inbred varieties. Further, these lines can be used in crosses for the commercial production of hybrid seeds capable of growing into plants having enhanced quality grain traits. Examples of such quality grain traits include, for example, oil content in excess of 6% of the seed dry matter, protein content in excess of 10% of the seed dry matter, improved oil quality, enhanced oxidative stability of the oil, reduced polyunsaturated fatty acids in the oil, oleic acid content in excess of 35% of the total fatty acids of the oil, lysine content in excess of 0.32% of the seed dry matter, and tryptophan content in excess of 0.08% of the seed dry matter.

In selecting a second plant to cross with REN 001, or a line derived therefrom for the purpose of developing novel inbred lines, it will typically be desired to choose those plants that either themselves exhibit one or more selected desirable characteristics or that exhibit the desired characteristic(s) when in hybrid combination. Examples of potentially desired characteristics include enhanced quality grain traits, greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size. Alternatively, a plant of the corn accession REN 001 or a variety derived therefrom may be crossed with a second, different plant for the purpose of producing hybrid seed that is sold to farmers for planting in commercial production fields. In this case, a second variety is selected that confers desirable characteristics when in hybrid combination with the first line.

Corn plants (*Zea mays* L.) can be crossed by either natural or mechanical techniques. Natural pollination occurs in corn when wind blows pollen from the tassels to the silks that protrude from the tops of the recipient ears. Mechanical pollination can be effected either by controlling the types of pollen that can blow onto the silks or by pollinating by hand.

In one embodiment, crossing may comprise the steps of:
(a) planting in pollinating proximity seeds of a first and a second parent corn plant;
(b) cultivating or growing the seeds of the first and second parent corn plants into plants that bear flowers;
(c) emasculating flowers of either the first or second parent corn plant, i.e., treating the flowers so as to prevent pollen production, or alternatively, using as the female parent a male sterile plant, thereby providing an emasculated parent corn plant;
(d) allowing natural cross-pollination to occur between the first and second parent corn plants;
(e) harvesting seeds produced on the emasculated parent corn plant; and, where desired,
(f) growing the harvested seed into a corn plant, preferably, a hybrid corn plant.

Parental plants are typically planted in pollinating proximity to each other by planting the parental plants in alternating rows, in blocks or in any other convenient planting pattern. Where the parental plants differ in timing of sexual maturity, it may be desired to plant the slower maturing plant first, thereby ensuring the availability of pollen from the male parent during the time at which silks on the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

At the time of flowering, in the event that accession REN 001 or a plant derived therefrom is employed as the male parent, the tassels of the other parental plant can be removed from all plants employed as the female parental plant to avoid self-pollination. The detasseling can be achieved manually but also can be done by machine, if desired. Alternatively, when the female parent corn plant comprises a cytoplasmic or nuclear gene conferring male sterility, detasseling may not be required. Additionally, a chemical gametocide may be used to sterilize the male flowers of the female plant. In this case, the parent plants used as the male may either not be treated with the chemical agent or may comprise a genetic factor that causes resistance to the emasculating effects of the chemical agent. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety.

Following emasculation, the plants are then typically allowed to continue to grow and natural cross-pollination occurs as a result of the action of wind, which is normal in the pollination of grasses, including corn. As a result of the emasculation of the female parent plant, all the pollen from the male parent plant is available for pollination because tassels, and thereby pollen bearing flowering parts, have been previously removed from all plants being used as a female in the hybridization. Of course, during this hybridization procedure, the parental varieties are grown such that they are isolated from other corn fields to minimize or prevent any accidental contamination of pollen from foreign sources. These isolation techniques are well within the skill of those skilled in this art.

Both parental corn plants may be allowed to continue to grow until maturity or the male rows may be destroyed after flowering is complete. Only the ears from the female parental plants are harvested to obtain seeds of a novel $F_1$ hybrid. The novel $F_1$ hybrid seed produced can then be planted in a subsequent growing season in commercial fields or, alternatively, advanced in breeding protocols for purposes of developing novel inbred lines.

Alternatively, in another embodiment of the invention, both first and second parent corn plants can come from the same corn plant, i.e., from the accession designated REN 001 or plants derived therefrom. Thus, any corn plant produced using a process of the present invention and accession REN 001 or plants grown therefrom forms a part of the current invention. As used herein, crossing can mean selfing, backcrossing, crossing to another or the same variety, crossing to populations, and the like. Therefore, all corn plants produced using the corn plant REN 001 and lines derived therefrom as a parent are within the scope of this invention.

A. Utilization of REN 001 as a Pollinator for Enhancing Kernel Quality Traits

One advantage of the corn accession REN 001 is that it possesses markedly enhanced quality grain traits relative to typical prior varieties. These traits can be conferred through crossing for the production of kernels and plants grown therefrom with enhanced quality traits. Such enhanced traits may include, for example, elevated oil content, elevated protein content, improved oil quality, enhanced oxidative stability of the oil, reduced polyunsaturated fatty acids in the oil, elevated oleic acid content, and improved nutritional quality of the protein as well as other traits. In particular embodiments of the invention, plants obtained can comprise one or more enhanced quality traits selected from the group consisting of: oil content in excess of 6% of the seed dry matter, protein content in excess of 10% of the seed dry matter, oleic acid content in excess of 35% of the total fatty acids of the oil, lysine content in excess of 0.32% of the seed dry matter and tryptophan content in excess of 0.08% of the seed dry matter. As demonstrated herein, such enhanced quality traits may be conferred in hybrid combination.

The accession REN 001 can also be used to confer enhanced quality grain traits by way of the xenia and/or metaxenia effect, in which quality traits of pollen affect the grain resulting from the pollinating. One method for exploiting the effect involves planting in pollinating proximity in a field corn seed of the accession REN 001 or a plant derived therefrom and corn seed of an agronomically elite variety. By allowing these plants to grow together, pollen of the accession REN 001 becomes available to pollinate the female flowers of the agronomically elite variety. The pollinating confers enhanced quality grain traits upon the kernels produced by the pollinating, but the yield of grain will otherwise approach that normally obtained using the agronomically elite "female" parent. Using such a technique, it was shown that corn accession REN 001 confers improved quality grain traits when REN 001 is used as a pollinator (Tables 6 and 7).

Preferably, the agronomically elite plant used for grain production is rendered male sterile to prevent self pollination. This can be achieved genetically, manually or chemically, as is described herein. It is preferable that the agronomically elite parent has a similar maturity date to the accession REN 001 or the variety derived therefrom to ensure coincidence of the availability of pollen and receptivity thereto. The resulting kernels can then be harvested from the plants.

TABLE 6

Oil Content in Grain From Hybrid Corn Plants Pollinated by REN 001 and Selected Varieties

| FEMALE POLLEN | HC33 × IH283 | LH192 × LH82 | LH195 × LH59 | LH198 × H168 | LH198 × LH185 | LH212 × LH204 | LH236 × LH286 | SELF |
|---|---|---|---|---|---|---|---|---|
| REN 001 | 9.19 | 10.02 | 8.13 | 9.66 | 7.63 | 8.06 | 9.22 | 18.36 |
| IL. HIGH PROTEIN UI 1976 (INC 1987) | 4.65 | 5.38 | 4.57 | 5.31 | 4.12 | 4.29 | 4.73 | 4.89 |
| IL. HIGH OIL UI 1975 (INC 1981) | 7.58 | 7.87 | 6.36 | 6.79 | 6.22 |  | 6.74 | 16.65 |
| IL HIGH PROTEIN UI 1964 (INC | 4.97 | 5.52 | 4.52 | 5.04 | 4.41 | 4.46 | 4.98 | 4.93 |
| IL. HIGH PROTEIN UI 1986 (INC 1987) | 4.98 | 5.00 | 4.52 | 4.86 | 4.18 | 4.24 | 5.18 | 4.25 |
| IL. REV. HIGH OIL UI 1994 BULK |  |  | 6.26 | 6.26 | 5.31 | 5.19 |  |  |
| IL. SWITCHBACK HIGH OIL UI 1995 BULK | 7.01 | 7.43 | 6.10 | 6.86 | 6.20 | 5.44 | 6.44 | 13.89 |

*Values are by wt %. These are typical values. Values may vary due to environment. Other values that are substantially equivalent are also within the scope of the invention.

TABLE 7

Quality Grain Traits in Hybrids Pollinated by REN 001 and Selected Hybrid Varieties

| FEMALE POLLEN | LH195 × LH59 REN 001 | LH195 × LH59 CUBA117 × B73 | LH236 × LH286 REN 001 | LH236 × LH286 CUBA117 × B73 | LH198 × LH185 REN 001 | LH198 × LH185 CUBA117 × B73 | REN 001 REN 001 |
|---|---|---|---|---|---|---|---|
| MOIST | 8.21 | 9.13 | 8.18 | 8.93 | 8.10 | 8.78 | 7.27 |
| CP | 14.56 | 13.66 | 13.55 | 14.24 | 15.48 | 9.14 | 13.65 |
| STARC | 59.35 | 67.25 | 60.64 | 67.69 | 58.18 | 70.01 | 49.28 |
| OIL | 8.13 | 4.11 | 9.22 | 4.03 | 7.63 | 4.03 | 18.36 |
| CYS | 0.30 | 0.278 | 0.266 | 0.280 | 0.332 | 0.201 | 0.302 |
| ASP | 0.945 | 0.860 | 0.925 | 0.869 | 0.996 | 0.600 | 0.882 |
| GLU | 2.877 | 2.871 | 2.852 | 2.958 | 3.163 | 1.700 | 2.561 |
| SER | 0.734 | 0.684 | 0.716 | 0.698 | 0.765 | 0.446 | 0.654 |
| HIST | 0.428 | 0.361 | 0.377 | 0.386 | 0.409 | 0.294 | 0.358 |
| GLY | 0.545 | 0.445 | 0.487 | 0.450 | 0.523 | 0.358 | 0.548 |
| THREN | 0.496 | 0.446 | 0.450 | 0.449 | 0.496 | 0.314 | 0.464 |
| METH | 0.322 | 0.254 | 0.265 | 0.256 | 0.356 | 0.183 | 0.393 |
| ARG | 0.775 | 0.641 | 0.706 | 0.634 | 0.789 | 0.482 | 0.802 |
| ALA | 1.073 | 1.038 | 1.070 | 1.066 | 1.168 | 0.644 | 0.984 |
| TYR | 0.568 | 0.533 | 0.557 | 0.557 | 0.620 | 0.340 | 0.525 |
| VAL | 0.727 | 0.642 | 0.687 | 0.656 | 0.745 | 0.434 | 0.663 |
| PHENY | 0.739 | 0.694 | 0.720 | 0.715 | 0.780 | 0.419 | 0.632 |
| ISO | 0.548 | 0.507 | 0.531 | 0.522 | 0.575 | 0.316 | 0.482 |
| LEU | 1.727 | 1.730 | 1.740 | 1.811 | 1.891 | 0.994 | 1.500 |
| LYS | 0.397 | 0.305 | 0.345 | 0.305 | 0.378 | 0.088 | 0.449 |
| TRYP | 0.110 | 0.091 | 0.110 | 0.088 | 0.116 | 0.076 | 0.120 |

*Values other than moisture are by wt %. These are typical values. Values may vary due to environment. Other values that are substantially equivalent are also within the scope of the invention.

B. Breeding of a REN 001-Derived Inbred Line With Enhanced Quality Grain Traits

As described herein above, the corn accession REN 001 may be used for the production of novel inbred corn varieties having enhanced quality grain traits. The breeding history of one such exemplary inbred plant derived from REN 001, designated HOI001, is set forth below. As can be seen, this plant exhibited markedly enhanced quality grain traits. The breeding history of HOI001 was as follows:

March 1997: Seed was obtained from the Maize Genetics Cooperative in Urbana, Ill. and seeds with large embryos were selected.

Summer 1997: Selected seeds were designated REN 001 and planted in Rows 32861 and 32862. Selections were made and plants were advanced on a bulk basis as plant and ear phenotype indicated the plants were already partially inbred, possibly equivalent to an S3 or S4 generation.

Winter 97–98: Selected plants were grown in Hawaii Nursery Rows 7556–7565. All plants were selfed and testcrosses were made for evaluation. Selected ears were advanced on a bulk basis. An increase of selected ears was planted in Hawaii Row 33724.

Summer 1998: Selected plants were grown in Iowa Nursery Rows 66619–66620. Five ears per row were selfed and testcrosses were made for evaluation. The ears appeared uniform.

Winter 98–99: Increase was planted in Hawaii rows 34091–34140.

Spring 1999: The seed from the increase was designated HOI001.

A physiological description of HOI001 was taken and is set forth below in Table 8.

TABLE 8

Physiological and Morphological Characteristics for the HOI001 Phenotype

| CHARACTERISTIC | VALUE |
| --- | --- |
| 1. PLANT | |
| Plant Height (cm) | 211.3 |
| Ear Height (cm) | 116.3 |
| Length of Top Ear Internode (cm) | 10.9 |
| Average Number of Tillers | 0.0 |
| Average Number of Ears per Stalk | 1.0 |
| Anthocyanin of Brace Roots | Absent |
| 2. LEAF | |
| Color | Medium Green |
| Leaf Angle (degrees) | 20.0 |
| Number of Leaves above Top Ear | 6.0 |
| Length cm. | 75.5 |
| Width cm. | 9.0 |
| Sheath Pubescence | Light |
| Marginal Waves | Many |
| Longitudinal Creases | Few |
| 3. TASSEL | |
| Branch Angle (degrees) | 22.0 |
| Length cm. | 36.3 |
| Pollen Shed | Heavy |
| Branch Number | 7.0 |
| Anther Color | Yellow |
| Glume Color | Green |
| Glume Band | Absent |
| 4. EAR | |
| Silk Color | Light Green |
| Taper | Slight |
| Position (attitude) | Upright |

TABLE 8-continued

Physiological and Morphological Characteristics for the HOI001 Phenotype

| CHARACTERISTIC | VALUE |
| --- | --- |
| Length cm. | 10.4 |
| Diameter cm. | 4.2 |
| Weight gm. | 48.6 |
| Shank Length cm. | 13.8 |
| Husk Extension cm. | Very Long (>10 cm) |
| Husk Tightness | Moderate |
| Husk Color Fresh | Medium Green |
| Husk Color Dry | Buff |
| Cob Diameter mm. | 31.6 |
| Cob Color | Red |
| 5. KERNEL | |
| Row Number | 16.0 |
| % Round Kernels | 28.7 |
| Row Direction | Straight |
| Kernel Rows | Distinct |
| Type | Flint |
| Aleurone Color Pattern | Homozygous |
| Aleurone Color | White |
| Length (depth) mm. | 10.0 |
| Width mm. | 8.1 |
| Thickness | 5.3 |
| Weight of 100K gm. | 20.4 |
| Endosperm Type | High Oil |
| Endosperm Color | Yellow |
| 6. MATURITY | |
| From Emergence to 50% of Plants in Silk | 1426.0 Heat Units - 71 Days |
| From Emergence to 50% of Plants in Pollen | 1399.0 Heat Units - 70 Days |
| 7. AGRONOMIC TRAITS | |
| Stay Green (at 65 days after anthesis) (scale: 1 = worst to 9 = excellent) | 7 |
| % Dropped Ears (at 65 days after anthesis) | 0.0 |
| % Pre-anthesis Brittle Snap | 0.0 |
| % Pre-anthesis Root Lodging | 30.0 |
| % Post-anthesis Root Lodging | 0.0 |

*These are typical values. Values may vary due to environment. Other values that are substantially equivalent are also within the scope of the invention.

The REN 001-derived variety HOI001 was also evaluated for quality grain traits, most notably, oil content in grain. HOI001 was evaluated both as an inbred and when in hybrid combination with selected inbred lines. As can be seen below in Tables 9–14, the inbred HOI001 has enhanced quality grain traits and these traits are conferred to hybrid corn plants having HOI001 as one inbred parent.

TABLE 9

Comparison of Hybrids Made Using HOI001 on % Dry Weight Basis

| Sample description | % Endosperm by dry wt | % Embryo by dry wt | % Oil in endosperm by dry wt | % Oil in embryo by dry wt | % Oil in kernel* by dry wt |
|---|---|---|---|---|---|
| HOI001 selfed | 67.7 | 32.3 | 4.04 | 59.28 | 21.88 |
| HOI001 × LH242 | 75.6 | 24.4 | 2.32 | 45.10 | 12.76 |
| LH242 × HOI001 | 81.7 | 18.3 | 1.59 | 49.71 | 10.40 |
| LH242 selfed | 89.0 | 11.0 | 0.62 | 33.88 | 4.28 |
| HOI001 × LH59 | 77.2 | 22.8 | 2.52 | 45.15 | 12.24 |
| LH59 × HOI001 | 82.5 | 17.5 | 1.54 | 44.72 | 9.10 |
| LH59 selfed | 88.0 | 12.0 | 0.66 | 33.23 | 4.57 |

*The weight of endosperm + embryo was used to represent kernel weight in this calculation.

TABLE 10

Comparison of Hybrids Made Using HOI001 on a Per Kernel Basis

| Sample description | Endosperm Size (mg) | Embryo Size (mg) | Endosperm + embryo (mg) | mg Oil in endosperm | mg Oil in embryo | mg Oil in endosperm + embryo |
|---|---|---|---|---|---|---|
| HOI001 selfed | 127.4 | 60.9 | 188.3 | 5.15 | 36.10 | 41.25 |
| HOI001 × LH242 | 140.1 | 45.1 | 185.2 | 3.25 | 20.34 | 23.59 |
| LH242 × HOI001 | 214.7 | 48.1 | 262.8 | 3.41 | 23.91 | 27.32 |
| LH242 selfed | 186.1 | 23.0 | 209.1 | 1.15 | 7.79 | 8.94 |
| HOI001 × LH59 | 154.7 | 45.7 | 200.4 | 3.90 | 20.63 | 24.53 |
| LH59 × HOI001 | 258.7 | 54.9 | 313.6 | 3.98 | 24.55 | 28.53 |
| LH59 selfed | 212.2 | 28.8 | 241.0 | 1.40 | 9.57 | 10.97 |

TABLE 11

Total Fatty Acid Methyl Ester (FAME) Duplicated Data for % Oil in Embryo by Dry Weight

| Sample description | Sample 1 (5 pooled seeds) | Sample 2 (5 pooled seeds) | Average |
|---|---|---|---|
| HOI001 selfed | 60.16 | 58.39 | 59.28 |
| HOI001 × LH242 | 45.21 | 44.99 | 45.10 |
| LH242 × HOI001 | 49.70 | 49.71 | 49.71 |
| LH242 selfed | 34.56 | 33.21 | 33.88 |
| HOI001 × LH59 | 44.86 | 45.44 | 45.15 |
| LH59 × HOI001 | 43.97 | 45.47 | 44.72 |
| LH59 selfed | 32.38 | 34.07 | 33.23 |

TABLE 12

Enhancement of Oil Content in Three-Way Hybrids with HOI001

| Pedigree | Yield (Bu/A) | Grain Moisture (%) | Stalk Lodging (%) | Root Lodging (%) | Oil Content (%) |
|---|---|---|---|---|---|
| LH310 × RQ0084 | 172.5 | 20.5 | 4.6 | 4.5 | 5.8 |
| (LH310 × HOI001) × RQ0084 | 136.2 | 19.8 | 5.8 | 18.7 | 9.5 |
| LH310 × RQ0085 | 177.7 | 25.5 | 2.8 | 5.4 | 6.1 |
| (LH310 × HOI001) × RQ0085 | 127.9 | 25.3 | 8.8 | 8.6 | 9.3 |

TABLE 13

Comparison of Conventional Hybrids to a Hybrid of HOI001

| Pedigree | Yield (Bu/A) | Grain Moisture (%) | Stalk Lodging (%) | Root Lodging (%) | Oil Content (%) |
|---|---|---|---|---|---|
| (HC33 × LH198) × LH59 | 127.5 | 18.1 | 13.5 | 0.0 | 4.2 |
| (HC33 × LH198) × LH185 | 149.5 | 19.1 | 6.1 | 2.4 | 4.3 |
| (HC33 × LH198) × LH283 | 143.2 | 19.9 | 13.0 | 3.5 | 4.7 |
| (HC33 × LH198) × HOI001 | 115.0 | 18.7 | 18.3 | 4.2 | 9.0 |

TABLE 14

Comparison of Conventional Hybrids to a Hybrid of HOI001

| Pedigree | Yield (Bu/A) | Grain Moisture (%) | Stalk Lodging (%) | Root Lodging (%) | Oil Content (%) |
|---|---|---|---|---|---|
| (LH227 × LH228) × LH82 | 175.5 | 18.0 | 21.2 | 11.8 | 4.5 |
| (LH227 × LH228) × LH172 | 172.7 | 17.1 | 14.8 | 12.8 | 4.0 |
| (LH227 × LH228) × LH176 | 192.5 | 16.8 | 6.0 | 7.0 | 3.9 |
| (LH227 × LH228) × HOI001 | 193.5 | 17.6 | 11.5 | 16.5 | 9.0 |

The variety designated HOI002 was also produced using REN 001 in accordance with the invention. A description of the physiological and morphological characteristics of corn plant HOI002 is given in Table 15.

TABLE 15

Physiological and Morphological Traits for HOI002

| MATURITY: | Days | Heat Units |
|---|---|---|
| From emergence to 50% of plants in silk: | 80 | 1524 |
| From emergence to 50% of plants in pollen | 79 | 1496 |

$$\text{Heat Units:} = \frac{[\text{Max. Temp.} (\leq 86°\text{F.}) + \text{Min. Temp..}(\geq 50°\text{F.})]}{2} - 50$$

PLANT:

Plant Height (to tassel tip): 206.0 cm
Ear Height (to base of top ear): 112.0 cm
Average number of Tillers: 0
Average Number of Ears per Stalk: 1
Anthocyanin of Brace Roots: Absent

LEAF:

Width of Ear Node Leaf: 9.0 cm
Length of Ear Node Leaf: 72.0 cm
Number of leaves above top ear: 5
Leaf Angle (from 2nd Leaf above ear at anthesis to Stalk above leaf): 27°
Leaf Color: Medium Green—Munsell Color Code 5 GY 4/4
Leaf Sheath Pubescence (Rate on scale from 1 = none to 9 = like peach fuzz): 2
Marginal Waves (Rate on scale from 1 = none to 9 = many): 4
Longitudinal Creases (Rate on scale from 1 = none to 9 = many): 5

TASSEL:

Number of Lateral Branches: 4
Branch Angle from Central Spike: 15°
Tassel Length (from top leaf collar to tassel top): 39.0 cm
Pollen Shed (Rate on scale from 0 = male sterile to 9 = heavy shed): 6
Anther Color: Green-Yellow—Munsell Color Code 2.5 GY 8/10
Glume Color: Green—Munsell Color Code 5 GY 5/8
Bar Glumes: Absent EAR: (Unhusked Data)

Silk Color (3 days after emergence): Light Green—Munsell Color Code 2.5 GY 8/6
Fresh Husk Color (25 days after 50% silking): Light Green—Munsell Color Code 2.5 GY 7/8
Dry Husk Color (65 days after 50% silking): Buff—Munsell Color Code 7.5 YR 7/4
Husk Extension: Short (ears exposed)

EAR: (Husked Ear Data)

Ear Length: 12.0 cm
Ear Diameter at mid-point: 42.0 mm
Ear Weight: 66.0 gm
Number of Kernel Rows: 18
Kernel Rows: Distinct
Shank Length: 10.0 cm
Ear Taper: Average KERNEL: (Dried)

Kernel Length: 10.0 mm
Kernel Width: 7.0 mm

TABLE 15-continued

Physiological and Morphological Traits for HOI002

Kernel Thickness: 4.0 mm
Round Kernels (Shape Grade):
Aleurone Color Pattern: Homozygous

COB:

Cob Diameter at Mid-Point: 3.1

*These are typical values. Values may vary due to environment. Other values that are substantially equivalent are also within the scope of the invention.

The REN 001-derived variety HOI002 was also evaluated for quality grain and other traits, most notably, oil content in grain. As can be seen below in Tables 16–18, the inbred HOI002 confers enhanced quality grain traits to hybrid corn plants having HOI002 as a parent.

TABLE 16

Enhancement of Oil Content in Three-Way Hybrids with HOI002

| Pedigree | Yield (Bu/A) | Grain Moisture (%) | Stalk Lodging (%) | Root Lodging (%) | Oil Content (%) |
|---|---|---|---|---|---|
| LH310 × RQ0084 | 172.5 | 20.5 | 4.6 | 4.5 | 5.8 |
| (LH310 × HOI002) × RQ0084 | 131.1 | 20.1 | 7.0 | 16.7 | 9.8 |
| LH310 × RQ0085 | 177.7 | 25.5 | 2.8 | 5.4 | 6.1 |
| (LH310 × HOI001) × RQ0085 | 156.5 | 23.7 | 7.3 | 4.5 | 8.9 |

TABLE 17

Comparison of Conventional Hybrids to a Hybrid of HOI002

| Pedigree | Yield (Bu/A) | Grain Moisture (%) | Stalk Lodging (%) | Root Lodging (%) | Oil Content (%) |
|---|---|---|---|---|---|
| (LH227 × LH228) × LH82 | 175.5 | 18.0 | 21.2 | 11.8 | 4.5 |
| (LH227 × LH228) × LH172 | 172.7 | 17.1 | 14.8 | 12.8 | 4.0 |
| (LH227 × LH228) × LH176 | 192.5 | 16.8 | 6.0 | 7.0 | 3.9 |
| (LH227 × LH228) × HOI002 | 173.7 | 17.8 | 9.3 | 17.0 | 9.8 |

TABLE 18

Comparison of Conventional Hybrids to a Hybrid of HOI002

| Pedigree | Yield (Bu/A) | Grain Moisture (%) | Stalk Lodging (%) | Root Lodging (%) | Oil Content (%) |
|---|---|---|---|---|---|
| (HC33 × LHl98) × LH59 | 127.5 | 18.1 | 13.5 | 0.0 | 4.2 |
| (HC33 × LHl98) × LH185 | 149.5 | 19.1 | 6.1 | 2.4 | 4.3 |
| (HC33 × LH198) × LH283 | 143.2 | 19.9 | 13.0 | 3.5 | 4.7 |
| (HC33 × LH198) × HOI002 | 128.2 | 20.3 | 11.2 | 13.4 | 9.9 |

C. Hybrid Corn Plant and Seed Production

Any time the accession REN 001 or a variety derived therefrom is crossed with another, different corn plant, a first generation ($F_1$) corn hybrid plant is produced. As such, an $F_1$ hybrid corn plant may be produced by crossing accession REN 001, or a variety derived therefrom, with any second maize plant. The goal of the process of producing an $F_1$ hybrid is to manipulate the genetic complement of corn to generate new combinations of genes that interact to yield new or improved traits (phenotypic characteristics). A process of producing a new $F_1$ hybrid typically begins with the production of one or more inbred plants. Those plants are produced by repeated crossing of ancestrally related corn plants to try to combine certain genes within the inbred plants.

Corn has a diploid phase, which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Inbreeding requires sophisticated manipulation by human breeders. Even in the extremely unlikely event that inbreeding rather than crossbreeding occurred in natural corn, achievement of complete inbreeding cannot be expected in nature due to well known deleterious effects of homozygosity and the large number of generations the plant would have to breed in isolation. The reason for the breeder to create inbred plants is to have a known reservoir of genes whose gametic transmission is predictable. The development of inbred plants generally requires about 5 to 7 generations of selfing. Inbred plants are then cross-bred in an attempt to develop improved $F_1$ hybrids. Hybrids are then screened and evaluated in small scale field trials. Typically, about 10 to 15 phenotypic traits, selected for their potential, commercial value, are measured.

When a plant of the accession REN 001, or of a variety derived therefrom, is crossed with another plant to yield a hybrid, the plant can serve as either the maternal or paternal plant. For many crosses, the outcome is the same regardless of the assigned sex of the parental plants. However, there is often one of the parental plants that is preferred as the maternal plant because of increased seed yield and production characteristics. Some plants produce tighter ear husks leading to more loss, for example, due to rot. There can be delays in silk formation that deleteriously affect timing of the reproductive cycle for a pair of parental plants. Seed coat characteristics can be preferable in one plant. Pollen can be shed better by one plant. Other variables can also affect preferred sexual assignment of a particular cross. In the instant case, it was generally preferable to use REN 001 and lines derived therefrom as the male parent.

IV. Single Locus Conversions

When the term corn plant is used in the context of the present invention, this also includes any single locus conversions of that corn plant. The term single locus converted plant as used herein refers to those corn plants that are developed by a plant breeding technique called backcrossing, wherein essentially all of the desired morphological and physiological characteristics of a variety are recovered in addition to the single locus transferred into the variety via the backcrossing technique. Backcrossing methods can be used with the present invention to improve or introduce a characteristic into the variety. The term backcrossing as used herein refers to the repeated crossing of a hybrid progeny back to one of the parental corn plants for that variety. The parental corn plant that contributes the locus or loci for the desired characteristic is termed the nonrecurrent or donor parent. This terminology refers to the fact that the nonrecurrent parent is used one time in the backcross protocol and therefore does not recur.

The parental corn plant to which the locus or loci from the nonrecurrent parent are transferred is known as the recurrent parent as it is used for several rounds in the backcrossing protocol (Poehlman et al., 1995; Fehr, 1987; Sprague and Dudley, 1988). In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred locus from the nonrecurrent parent. The backcross process may be accelerated by the use of genetic markers, such as SSR, RFLP, SNP or AFLP markers, to identify plants with the greatest genetic complement from the recurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single locus traits have been identified that are not regularly selected for in the development of a new inbred but that can be improved by backcrossing techniques. Single locus traits may or may not be transgenic; examples of these traits include, but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus, but may be inherited through the cytoplasm. Some known exceptions to this are genes for male sterility, some of which are inherited cytoplasmically, but still act as single locus traits. A number of exemplary single locus traits are described in, for example, PCT Application WO 95/06128, the disclosure of which is specifically incorporated herein by reference.

Examples of genes conferring male sterility include those disclosed in U.S. Pat. Nos. 3,861,709, 3,710,511, 4,654,465, 5,625,132, and 4,727,219, each of the disclosures of which are specifically incorporated herein by reference in their entirety. Where one desires to employ male-sterility systems with a corn plant in accordance with the invention, it may be beneficial to also utilize one or more male-fertility restorer genes. For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the corn plant is utilized, e.g., for silage, but in most cases, the seeds will be deemed the most valuable portion of the crop, so fertility of the hybrids in these crops must be restored. Examples of male-sterility genes and corresponding restorers that could be employed with the invention are well known to those of skill in the art of plant breeding and are disclosed in, for instance, U.S. Pat. Nos. 5,530,191; 5,689,041; 5,741,684; and 5,684,242, the disclosures of which are each specifically incorporated herein by reference in their entirety.

Direct selection may be applied where a single locus acts as a dominant trait. An example of a dominant trait is a herbicide resistance trait. For this selection process, the progeny of the initial cross are sprayed with the herbicide prior to the backcrossing. The spraying eliminates any plants that do not have the desired herbicide resistance characteristic, and only those plants that have the herbicide resistance gene are used in the subsequent backcross. This process is then repeated for all additional backcross generations.

Many useful single locus traits are those that are introduced by genetic transformation techniques. Methods for the genetic transformation of maize are known to those of skill in the art. For example, methods that have been described for the genetic transformation of maize include electroporation (U.S. Pat. No. 5,384,253), electrotransformation (U.S. Pat. No. 5,371,003), microprojectile bombardment (U.S. Pat. Nos. 5,550,318; 5,736,369, 5,538,880; and PCT Publication WO 95/06128), *Agrobacterium*-mediated transformation (U.S. Pat. No. 5,591,616 and E.P. Publication EP672752), direct DNA uptake transformation of protoplasts (Omirulleh et al., 1993) and silicon carbide fiber-mediated transformation (U.S. Pat. Nos. 5,302,532 and 5,464,765).

A type of single locus trait that can be introduced by genetic transformation (U.S. Pat. No. 5,554,798) and has particular utility is a gene that confers resistance to the herbicide glyphosate. Glyphosate inhibits the action of the enzyme EPSPS, which is active in the biosynthetic pathway of aromatic amino acids. Inhibition of this enzyme leads to starvation for the amino acids phenylalanine, tyrosine, and tryptophan and secondary metabolites derived therefrom. Mutants of this enzyme are available that are resistant to glyphosate. For example, U.S. Pat. No. 4,535,060 describes the isolation of EPSPS mutations that confer glyphosate resistance upon organisms having the *Salmonella typhimurium* gene for EPSPS, aroA. A mutant EPSPS gene having similar mutations has also been cloned from *Zea mays*. The mutant gene encodes a protein with amino acid changes at residues 102 and 106 (PCT Publication WO 97/04103). When a plant comprises such a gene, a herbicide resistant phenotype results.

Plants having inherited a transgene comprising a mutated EPSPS gene may, therefore, be directly treated with the herbicide glyphosate without the result of significant damage to the plant. This phenotype provides farmers with the benefit of controlling weed growth in a field of plants having the herbicide resistance trait by application of the broad spectrum herbicide glyphosate. For example, one could apply the herbicide ROUNDUP™, a commercial formulation of glyphosate manufactured and sold by the Monsanto Company, over the top in fields where glyphosate resistant corn plants are grown. The herbicide application rates may typically range from 4 ounces of ROUNDUP™ to 256 ounces ROUNDUP™ per acre. More preferably, about 16 ounces to about 64 ounces per acre of ROUNDUP™ may be applied to the field. However, the application rate may be increased or decreased as needed, based on the abundance and/or type of weeds being treated. Additionally, depending on the location of the field and weather conditions, which will influence weed growth and the type of weed infestation, it may be desirable to conduct further glyphosate treatments. The second glyphosate application will also typically comprise an application rate of about 16 ounces to about 64 ounces of ROUNDUP™ per acre treated. Again, the treatment rate may be adjusted based on field conditions. Such methods of application of herbicides to agricultural crops are well known in the art and are summarized in general in Anderson (1983).

Alternatively, more than one single locus trait may be introgressed into a variety by the method of backcross conversion. A selectable marker gene and a gene encoding a protein that confers a trait of interest may be simultaneously introduced into a maize plant as a result of genetic transformation. Usually one or more introduced genes will integrate into a single chromosome site in the host cell's genome. For example, a selectable marker gene encoding phosphinothricin acetyl transferase (PPT) (e.g., a bar gene) and conferring resistance to the active ingredient in some herbicides by inhibiting glutamine synthetase, and a gene encoding an endotoxin from *Bacillus thuringiensis* (Bt) and conferring resistance to particular classes of insects, e.g., lepidopteran insects, in particular the European Corn Borer, may be simultaneously introduced into a host genome. Furthermore, through the process of backcross conversion more than one transgenic trait may be transferred into an elite inbred.

The waxy characteristic is an example of a recessive trait. In this example, the progeny resulting from the first backcross generation (BC 1) must be grown and selfed. A test is then run on the selfed seed from the BC1 plant to determine which BC1 plants carried the recessive gene for the waxy trait. In other recessive traits additional progeny testing, for example growing additional generations such as the BC1S1, may be required to determine which plants carry the recessive gene.

V. Origin and Breeding History of an Exemplary Single Locus Converted Plant

Methods for the preparation of single gene converted plants are known to those of skill in the art. An example of such a single gene converted plant is 85DGD1 MLms, which is a single locus conversion of the corn line 85DGD1 to cytoplasmic male sterility. The methods used to convert this line were described in U.S. Pat. No. 6,175,063, the disclosure of which is incorporated herein in the entirety, and are set forth herein below. As described in U.S. Pat. No. 6,175,063, 85DGD1 MLms was derived using backcross methods. In particular, the line designated 85DGD1 was used as the recurrent parent and MLms, a germplasm source carrying ML cytoplasmic sterility, was used as the nonrecurrent parent. The breeding history of the single locus converted inbred 85DGD1 MLms can be summarized as follows:

| | |
|---|---|
| Hawaii Nurseries Planting Date Apr. 02, 1992 | Made up S-O: Female row 585 male row 500 |
| Hawaii Nurseries Planting Date Jul. 15, 1992 | S-O was grown and plants were backcrossed times 85DGD1 (rows 444' 443) |
| Hawaii Nurseries Planting Date Nov. 18, 1992 | Bulked seed of the BC1 was grown and backcrossed times 85DGD1 (rows V3-27' V3-26) |
| Hawaii Nurseries Planting Date Apr. 02, 1993 | Bulked seed of the BC2 was grown and backcrossed times 85DGD1 (rows 37' 36) |
| Hawaii Nurseries Planting Date Jul. 14, 1993 | Bulked seed of the BC3 was grown and backcrossed times 85DGD1 (rows 99' 98) |
| Hawaii Nurseries Planting Date Oct. 28, 1993 | Bulked seed of BC4 was grown and backcrossed times 85DGD1 (rows KS-63' KS-62) |
| Summer 1994 | A single ear of the BC5 was grown and backcrossed times 85DGD1 (MC94-822' MC94-822-7) |
| Winter 1994 | Bulked seed of the BC6 was grown and backcrossed times 85DGD1 (3Q-1' 3Q-2) |
| Summer 1995 | Seed of the BC7 was bulked and named 85DGD1 MLms. |

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

Anderson, W. P., Weed Science Principles, West Publishing Company, 1983.

Armstrong and Green, "Establishment and maintenance of friable, embryogenic maize callus and the involvement of L-proline," *Planta,* 164:207–214, 1985.

Conger, Novak, Afza, Erdelsky, "Somatic Embryogenesis from Cultured Leaf Segments of *Zea Mays,*" *Plant Cell Reports,* 6:345–347, 1987.

Duncan et al., "The Production of Callus Capable of Plant Regeneration from Immature Embryos of Numerous *Zea Mays* Genotypes," *Planta,* 165:322–332, 1985.

Fehr, "Theory and Technique," In: *Principles of Cultivar Development,* 1:360–376, 1987.

Gaillard et al., "Optimization of Maize Microspore Isolation and Culture Condition for Reliable Plant Regeneration," *Plant Cell Reports,* 10(2):55, 1991.

Gordon-Kamm et al., "Transformation of Maize Cells and Regeneration of Fertile Transgenic Plants," *The Plant Cell,* 2:603–618, 1990.

Green and Rhodes, "Plant Regeneration in Tissue Cultures of Maize: Callus Formation from Stem Protoplasts of Corn (*Zea Mays* L.)," In: *Maize for Biological Research,* 367–372, 1982.

Jensen, "Chromosome Doubling Techniques in Haploids," *Haploids and Higher Plants—Advances and Potentials, Proceedings of the First International Symposium,* 1974.

Nienhuis et al., "Restriction Fragment Length Polymorphism Analysis of Loci Associated with Insect Resistance in Tomato," *Crop Science,* 27(4):797–803, 1987.

Omirulleh et al., "Activity of a chimeric promoter with the doubled CaMV 35S enhancer element in protoplast-derived cells and transgenic plants in maize," *Plant Mol. Biol.,* 21(3):415–428, 1993.

Pace et al., "Anther Culture of Maize and the Visualization of Embryogenic Microspores by Fluorescent Microscopy," *Theoretical and Applied Genetics,* 73:863–869, 1987.

Poehlman et al., "Breeding Field Crops," 4th Ed., Iowa State University Press, Ames, Iowa, pp 132–155 and 321–344, 1995.

Rao et al., "Somatic Embryogenesis in Glume Callus Cultures," *Maize Genetics Cooperation Newsletter,* 60, 1986.

Songstad et al., "Effect of 1-Aminocyclopropate-1-Carboxylic Acid, Silver Nitrate, and Norbornadiene on Plant Regeneration from Maize Callus Cultures," *Plant Cell Reports,* 7:262–265, 1988.

Sprague and Dudley (eds.), "Corn and Corn improvement," 3rd Ed., Crop Science of America, Inc., and Soil Science of America, Inc., Madison Wis. pp 881–883 and pp 901–918, 1988.

Stuber et al., "Techniques and scoring procedures for starch gel electrophoresis of enzymes of maize C. *Zea mays,* L.," *Tech. Bull.,* 286, 1988.

Wan et al., "Efficient Production of Doubled Haploid Plants Through Colchicine Treatment of Anther-Derived Maize Callus," *Theoretical and Applied Genetics,* 77:889–892, 1989.

Wang et al., "Large-Scale Identification, Mapping, and Genotyping of Single-Nucleotide Polymorphisms in the Human Genome," *Science,* 280:1077–1082, 1998.

Williams et al., "Oligonucleotide Primers of Arbitrary Sequence Amplify DNA Polymorphisms which Are Useful as Genetic Markers," *Nucleic Acids Res.,* 18:6531–6535, 1990.

What is claimed is:

1. A method of producing a corn plant with at least one improved quality grain trait comprising the steps of:
    (a) crossing a corn plant of corn accession REN 001 with a second corn plant or with itself, wherein a sample of seed of corn accession REN 001 was deposited under ATCC Accession No. PTA-3822; and
    (b) selecting a progeny corn plant resulting from said crossing and having at least one improved quality grain trait.

2. The method of claim 1, wherein crossing comprises rendering the corn plant of corn accession REN 001 or the second corn plant male sterile prior to said crossing.

3. The method of claim 2, wherein rendering the corn plant of corn accession REN 001 or the second corn plant male sterile comprises introducing a nuclear or cytoplasmic gene conferring male sterility or detasseling prior to said crossing.

4. The method of claim 1, wherein crossing comprises hand pollinating or allowing natural pollination to occur.

5. The method of claim 1, wherein the improved quality grain trait is selected from the group consisting of: oil content in excess of about 6% of the seed dry matter, protein content in excess of about 10% of the seed dry matter, oleic acid content in excess of about 35% of the total fatty acids of the oil, lysine content in excess of about 0.32% of the seed dry matter and tryptophan content in excess of about 0.08% of the seed dry matter.

6. The method of claim 1, wherein the second corn plant is a plant of the corn accession REN 001.

7. The method of claim 1, wherein the second corn plant is an inbred, a hybrid or a synthetic hybrid.

8. The method of claim 1, wherein the second corn plant is genetically heterogeneous.

9. The method of claim 1, wherein the corn plant of corn accession REN 001 is used as a pollen donor and the second corn plant is a pollen receptor or the corn plant of corn accession REN 001 is used as a pollen receptor and the second corn plant is a pollen donor.

10. The method of claim 1, further comprising the steps of:
    (c) crossing the progeny corn plant with itself or a third plant to produce a progeny plant of a subsequent generation comprising at least one improved quality grain trait.

11. The method of claim 10, further comprising the steps of:
    (d) crossing the progeny plant of a subsequent generation with itself or a second plant; and
    (e) repeating steps (c) and (d) for an additional 3–10 generations with selection for at least one improved quality grain trait to produce an inbred corn plant derived from the corn accession REN 001 and comprising at least one improved quality grain trait.

12. The method of claim 11, wherein said progeny plant of a subsequent generation is selected for crossing based on the presence of at least a first enhanced quality grain trait.

13. The method of claim 12, wherein the progeny plant of a subsequent generation is selected at each generation for crossing based on the presence of at least a first enhanced quality grain trait.

14. The method of claim 12, wherein the enhanced quality grain trait is selected from the group consisting of: oil content in excess of about 6% of the seed dry matter, protein content in excess of about 10% of the seed dry matter, oleic acid content in excess of about 35% of the total fatty acids of the oil, lysine content in excess of about 0.32% of the seed dry matter, and tryptophan content in excess of about 0.08% of the seed dry matter.

15. The method of claim 13, wherein the progeny plant of a subsequent generation is selected at each generation for crossing based on the presence of at least two enhanced quality grain traits selected from the group consisting of: oil content in excess of about 6% of the seed dry matter, protein content in excess of about 10% of the seed dry matter, oleic acid content in excess of about 35% of the total fatty acids of the oil, lysine content in excess of about 0.32% of the seed dry matter, and tryptophan content in excess of about 0.08% of the seed dry matter.

16. A process of producing corn grain, comprising:
    (a) planting seeds of first and second corn plants in pollinating proximity, wherein the first plant is an agronomically elite variety and wherein the second plant is a corn plant of the accession REN 001, wherein a sample of the seed of the corn accession REN 001 was deposited under ATCC Accession No. PTA-3822;
    (b) growing the first and second plants to sexual maturity;
    (c) allowing pollen from the second plant to pollinate the first plant; and
    (d) collecting grain that forms on at least the first plant.

17. The process of claim 16, further defined as comprising planting a population of seeds of said first and second corn plants.

18. The process of claim 16, wherein collecting comprises harvesting grain formed on the first corn plant and the second corn plant.

19. The process of claim 16, wherein the first corn plant is rendered male sterile by genetic, chemical or mechanical means.

20. The process of claim 16, wherein the first corn plant is genetically male sterile.

* * * * *